(12) United States Patent
Powell et al.

(10) Patent No.: US 7,892,781 B2
(45) Date of Patent: Feb. 22, 2011

(54) DETECTING A TARGET USING A COMPOSITE PROBE COMPRISING A DIRECTING AGENT, A METAL NANOPARTICLE AND AN ENZYME

(75) Inventors: Richard D. Powell, Raleigh, NC (US); Vishwas N. Joshi, East Setauket, NY (US); James F. Hainfeld, Shoreham, NY (US)

(73) Assignee: Nanoprobes, Inc., Yaphank, NY (US)

( * ) Notice: Subject to any disclaimer, the term of this patent is extended or adjusted under 35 U.S.C. 154(b) by 172 days.

(21) Appl. No.: 12/150,379

(22) Filed: Apr. 28, 2008

(65) Prior Publication Data

US 2008/0318249 A1 Dec. 25, 2008

Related U.S. Application Data (63) Continuation-in-part of application No. 11/121,484, filed on May 4, 2005, now Pat. No. 7,364,872, which is a continuation-in-part of application No. 10/658,609, filed on Sep. 8, 2003, now Pat. No. 7,183,072, which is a continuation-in-part of application No. 09/822,131, filed on Mar. 30, 2001, now Pat. No. 6,670,113.

(51) Int. Cl.
*C12Q 1/28* (2006.01)
(52) U.S. Cl. .................. 435/28; 435/7.72; 424/46
(58) Field of Classification Search .............. 435/28, 435/7.72; 424/46
See application file for complete search history.

(56) References Cited

U.S. PATENT DOCUMENTS

| | | | |
|---|---|---|---|
| 5,116,734 A | 5/1992 | Higgs et al. | 435/28 |
| 5,595,878 A | 1/1997 | Sood et al. | 435/6 |
| 6,358,682 B1 | 3/2002 | Jaffee et al. | 435/6 |
| 6,369,206 B1 | 4/2002 | Leone et al. | 530/391.5 |
| 6,534,039 B2 | 3/2003 | Hainfeld | 424/9.32 |
| 6,670,113 B2 * | 12/2003 | Hainfeld | 435/4 |
| 0,074,457 A1 | 4/2005 | Kamal et al. | 424/155.1 |
| 6,911,306 B1 | 6/2005 | Vertino | 435/6 |
| 7,183,072 B1 * | 2/2007 | Hainfeld | 435/25 |
| 7,364,872 B1 * | 4/2008 | Hainfeld | 435/25 |
| 2004/0253624 A1 | 12/2004 | Smith et al. | 435/6 |
| 2005/0100976 A1 | 5/2005 | Bieniarz et al. | 435/7.92 |

OTHER PUBLICATIONS

Powell R. et al. Combined Fluorescent and Gold Probes for Microscopic and Morphological Investigations. Gold and Silver Staining. Editor Hacker, G. CRC Press Boca Raton FL, pp. 107-118, 2002.*
Powell R. et al. Metallographic in situ Hybridization. Human Pathology 38(8)1145-1159, Aug. 2007.*

* cited by examiner

*Primary Examiner*—Ralph Gitomer
(74) *Attorney, Agent, or Firm*—Klarquist Sparkman, LLP (57) ABSTRACT

A test agent includes a composite probe having at least one nanoparticle having multiple metal atoms, a directing agent, and an enzyme. The directing agent attaches the probe to a target in a test sample. The test sample and bound probe are then treated with an enzyme substrate. A method of detecting a target in a test sample includes exposing the test sample to the probe, then treating the test sample with an enhancement or development solution to deposit at least one of a fluorophore, a chromogen, or a metal.

21 Claims, 6 Drawing Sheets

DETECTING A TARGET USING A COMPOSITE PROBE COMPRISING A DIRECTING AGENT, A METAL NANOPARTICLE AND AN ENZYME

CROSS-REFERENCE TO RELATED APPLICATIONS

This application is a continuation-in-part of U.S. patent application Ser. No. 11/121,484, filed May 4, 2005, now U.S. Pat. No. 7,364,872, which is a continuation-in-part of U.S. patent application Ser. No. 10/658,609, filed Sep. 8, 2003, now U.S. Pat. No. 7,183,072, which is a continuation-in-part of U.S. patent application Ser. No. 09/822,131, filed Mar. 30, 2001, now U.S. Pat. No. 6,670,113, the contents of each of which are incorporated by reference in their entirety.

ACKNOWLEDGMENT OF GOVERNMENT SUPPORT

This invention was made with government support under grant Numbers 5R01AI031788-15, and 2R44GM064257-02A1 awarded by the National Institutes of Health. The federal government has certain rights in the invention.

FIELD

This disclosure relates generally to materials and methods for the detection and staining of targets. More particularly, the present disclosure relates to materials and methods for the detection and staining of biological components, disease markers, and markers for biological processes in cells or tissues, and any other specific chemical entities that may be targeted using a probe with a chemically or biologically specific affinity or localized microscopically.

BACKGROUND

Full understanding of the structure and function of a biological system requires a variety of structural information at a variety of levels of resolution. Rational understanding of biological systems and disease processes requires detection of the distribution, abundance, localization and function of biological molecules and processes at the cellular, subcellular and macromolecular level.

A wide variety of biological labeling and staining methods are available for detecting and localizing biological targets, each with advantages and limitations which suit it to different applications. In addition, the practice of molecular medicine depends upon accurate and reliable methods for the laboratory assessment of the presence, amount, distribution, density, and form of target analytes, both by eye using methods such as Western blotting, Southern and Northern blotting, gel staining, and immunoblotting, and microscopically using light and electron microscopy to evaluate the cellular distribution of targets such as genes by in situ hybridization, proteins by immunohistochemistry, and other molecules including but not restricted to hormones, carbohydrates, enzymes, and peptides. This is accomplished by a variety of processes that use a probe, targeted to the entity under consideration, attached to a label which then generates, either through its intrinsic properties or by specific interaction with other components applied subsequently, a signal which is detected, quantitated, or mapped to identify the presence, locations and amounts of the target.

Examples of probes include antibodies that react with a specific protein, oligonucleotides that are complementary to a genetic target, peptides that bind to specific protein subunits, or substrates that react with a target enzyme. A wide variety of methods are used for target visualization: these include fluorescent labels; particulate labels such as colloidal gold or other metals, which may be visualized directly by electron microscopy, or enlarged or rendered visible by light microscopy by other optical methods, or directly by eye through the deposition of additional metal from solution by autometallography; other intensely colored particles such as selenium or colored latex; or radionuclides that are used to expose film placed in proximity to the specimen. Enzymes targeted to the site of interest are widely used to visualize the target by treatment and reaction with a chromogenic substrate which develops color upon reaction with the enzyme. They may also be used to generate a signal indirectly, by the in situ generation of multiple copies of a target (for example, the polymerase chain reaction), the generation or deposition of multiple copies of a signal generating entity such as a fluorescently labeled substrate, or the deposition of multiple copies of a secondary target, such as biotinylated tyramide which is then visualized using a biotin-binding probe. These may be either linked to the probe directed against the target, or conjugated to a secondary, tertiary or other probe that is bound to the target in a subsequent step, either by reaction with the primary probe, or through an intermediate bridging or linking step.

Although metallographic labeling and detection, both using autometallographically enhanced gold particles and using enzyme metallography, affords greater sensitivity and specificity than many other detection methods for the optical and microscopic imaging of targets, the nature of the deposited metal means that the signal always appears as a black, completely opaque signal. If the visualization of a second overlapping target is required, visualization of this second target will be obscured by the metallographic signal. For example, enzyme metallography (EnzMet™) has achieved both ultrasensitive, high-resolution detection and localization of individual gene copies by conventional brightfield microscopy in situ hybridization, and highly sensitive and specific histochemical staining of target proteins in paraffin-embedded tissue sections. However, its application to spectral imaging and other automated imaging methods has been limited because the black signal does not give an identifiable spectrum, and therefore may be difficult to resolve from overlapping stains.

The current development and future practice of biomedical research and molecular medicine will increasingly require the detection and spatial evaluation of multiple targets simultaneously in order to study and evaluate relationships between components of a system, or to evaluate a series of different markers whose combined pattern of expression indicates the biologic behavior of the system under study or provides a prognosis for a disease process. In order to do so, methods to separate and resolve the signals used to visualize combinations of targets are required in order to accurately assess each target. This is usually achieved by the use of different colors; an example is the use of different colored fluorescent labels to assess both a target gene and a control gene, or to combine gene and protein assessment. While the human eye can resolve a small number of colors, an important advance is the use of spectroscopic image analysis ("spectral imaging") and related methods, in which the spectral signature of each point within an image is resolved to differentiate the spectra of the dyes present, and thus enable the quantitation of overlapping multiple signals. In this way, even colors that appear similar or identical to the human eye may be resolved spectroscopically.

The combination of the increased sensitivity and resolution of metallographic detection, with the ability to detect multiple colors that is conferred by the use of colored substrates, would provide greatly improved accuracy in the evaluation of biologic and other targets. In color photography, silver is reacted with aromatic dye precursors, known as dye couplers, to produce intensely colored organic dyes. This procedure is known as dye coupling. This process has been applied to the development of colors from metallographic deposits used for the detection of biological or chemical targets on only two occasions: by Haase, in conjunction with radioisotope labeling in cultured cells, and by and Fritz, in the detection of silver-enhanced colloidal gold particles.

Correlation of information at different levels of resolution usually requires multiple labeling and detection experiments. These necessitate lengthy procedures, impose difficulties in correlating the different data sets, and may allow the structural integrity of the specimen to be compromised.

Larger gold labels pose a particular problem for correlative labeling. Their use in combined fluorescent gold probes is limited because they quench the fluorescence through resonance energy transfer; in order to preserve useful fluorescence, even 6 nm gold and fluorescent labels must be conjugated to separate antibodies. Furthermore, fluorescence microscopy is a darkfield method. Staining cannot easily be visualized in the context of tissue morphology: this can be a critical disadvantage for users such as pathologists, who much prefer to evaluate staining in the context of tissue morphology by conventional brightfield light microscopy.

SUMMARY

There is provided a test agent comprising a composite probe including at least one nanoparticle having multiple metal atoms, at least one directing agent, and a chemically linked enzyme. The directing agent is adapted to attach to a target in a biological sample. The test sample and bound probe are treated with an enzyme substrate.

The composite probe may further comprise a polymer member, with multiple nanoparticles being bound to the polymer member.

The enzyme substrate may be a fluorescent or fluorogenic material, a chromogenic material, or a metallographic material.

The metallographic material may be an oxidizing agent, a reducing agent and a metal ion source, and at least some of the metal ions are reduced to a zero oxidation state.

The directing agent may comprise an antibody, an antibody fragment, a single chain antibody, a peptide, a drug, a nucleic acid, an enzyme substrate, an organic compound, or a protein. The enzyme substrate may be a redox active enzyme.

There is also provided a method of detecting a target in a sample comprising exposing the sample to a composite probe, treating the sample with an enhancement or development solution to deposit at least one of a fluorophore, a chromogen, or a metal, and performing at least one test to detect fluorescence produced by the deposited fluorophore, color produced by the deposited chromogen, the metal atoms of the nanoparticle, or the deposited metal.

The method may further comprise examining the sample by electron microscopy or other metallic cluster particle or deposit detection or visualization method.

The method may further comprise examining the sample by electron microscopy, brightfield microscopy, fluorescent microscopy, directly visible signal without microscopy, or electrical detection.

The method may further comprise examining the sample by direct optical detection or by an optical recording device.

The method may further comprise examining the electrical properties of the deposited metal.

The method may further comprise immobilizing the target on a membrane or other surface.

If the enhancement or development solution deposits a fluorescent or fluorogenic substrate, the test may comprise examining the sample with fluorescence microscopy or other fluorescent detection device or method.

If the enhancement or development solution deposits a metallographic substrate, the test may comprise examining the sample with light microscopy, electron microscopy, or other microscopical method for detecting or visualizing deposited metal.

If the enhancement or development solution deposits an autometallographic reagent or an enzyme metallographic substrate, the test may comprise examining the sample with brightfield light microscopy.

BRIEF DESCRIPTION OF THE DRAWINGS

In FIG. 2a, a silver development substrate having no modifier was tested, providing clearly stained polar tubes. In FIG. 2b, a silver development substrate having a modifier containing 15% gum arabic was tested, providing clearly stained polar tubes and almost no observable background.

As shown in FIG. 3a, this is sufficient to produce faint staining by light microscopy. In addition, fluorescence microscopy shows a clear fluorescent signal, FIG. 3b. The specimens were then processed for electron microscopy. Cover glasses were removed and the slides rinsed in distilled water, dehydrated through a series of ethanol solutions (50%-100%) and infiltrated with Araldite 502 resin (EMS, PA) overnight. Marked areas were covered with BEEM capsules filled with resin, and embedded at 60° C. for 24 hours. Thin sections were cut, placed on copper grids, and stained with uranyl acetate and lead citrate. Samples were examined using an FEI Tecnai 12 transmission electron microscope. The polar tubes were clearly visible and showed specific staining with silver-enhanced Nanogold, FIGS. 3c and 3d.

FIGS. 4a, 4b, 4c, 4d, 4e, 4f, 4g illustrate the results of staining experiments for *Encephalitozoon hellem* microsporidian-infected cultured RK-13 cells. Staining was conducted using primary antibodies against or PTP-80 (FIGS. 4a, 4b, 4d, 4e) or PTP-55 (FIGS. 4c, 4f and 4g). After light microscope examination, areas of interest were marked on the back of the slides. The cover glasses were removed, and the slides rinsed in distilled water, dehydrated through a series of ethanol solutions (50%-100%) and infiltrated with Araldite 502 resin (EMS, PA) overnight. Marked areas were covered with BEEM capsules filled with resin, and embedded at 60° C. for 24 hours. Thin sections were stained with uranyl acetate and lead citrate, then examined using an FEI Tecnai 12 transmission electron microscope at 80 kV. Strong and specific polar tube staining was found upon examination by all four microscopic methods: fluorescence microscopy after development with Alexa Fluor 488 tyramides (FIGS. 4a and 4b), transmission electron microscopy both with development with metallographic silver substrate (FIGS. 4d and 4e) and without development with metallographic silver substrate (FIG. 4c), and by brightfield light microscopy after development with the silver metallographic substrate (FIG. 4g). Strong fluorescence was observed even in the presence of 5 nm gold.

DETAILED DESCRIPTION

The subject method facilitates performance of multiple tests without requiring multiple labeling and detection operations. For example, both a gold particle and an enzymatic label may be conjugated to a single antibody probe, thereby enabling enzymatic and gold labeling in a single procedure. The two labels may then be detected by separate tests.

The subject method also provides increased sensitivity for target detection. In a first example, a test sample treated with combined enzymatic and gold probes is then subjected to metallographic enhancement procedures, such as enzymatic metallography, to visualize targets in blots and in tissues. As described below, the combined enzymatic and gold labeled probe achieves higher detection sensitivities than either gold or enzymatically labeled probes. In a second example, the combined enzymatic and gold labeled probe may be polymerized, or multiple enzymatic and gold labeled probes may be conjugated to a larger polymer member, or "backbone", to further increase the sensitivity of detection.

The subject method may both facilitate correlation of information at different levels of resolution without requiring multiple labeling and detection operations and provide increased sensitivity for target detection. For example, a test sample to which combined enzymatic and gold probes have been bound may then be treated with a fluorescent or fluorogenic substrate such as a fluorescent tyramide. As described below, this results in the deposition of a fluorescent reaction product at distances of 10 nm to 100 nm from the probe. This is distance is sufficient to ensure fluorescence is not quenched, but not so great as to diminish light microscopic resolution. Fluorescent staining may then be correlated with electron microscopic localization of the gold particles. In an alternative, the test sample/combined enzymatic and gold probe is treated with a conventional organic enzyme chromogen. This results in the deposition of a colored reaction product. Brightfield chromatic staining may then be correlated with electron microscopic localization of the gold particles, providing a correlative method that indicates target distribution in the context of underlying tissue morphology at both the light and electron microscopic level.

Disclosed are reagents and methods for targeted, correlative fluorescence or brightfield optical staining and electron microscopic labeling with gold nanoparticles 0.8 to 100 nm or larger in diameter. These new reagents comprise an antibody, protein, or other targeted biomolecule conjugated with both a gold nanoparticle of 1.4, 3, 5, 10 nm or larger diameter, and a redox active enzyme such as horseradish peroxidase. When bound to targets in cells and tissue specimens, these reagents may catalytically deposit fluorescent enzyme substrates to develop a specific fluorescence signal which is visualized and localized by fluorescence microscopy. Alternatively, they may catalyze the deposition of an organic chromogen to yield a colored stain which is visualized by brightfield light microscopy. Alternatively, the bound probes may be developed with either autometallographic reagents, which selectively deposit additional silver, gold, or other metal from solution onto the gold nanoparticles; or with enzyme metallographic substrates, which reacts with the redox enzyme to form a localized metallic deposit which is visualized by brightfield light microscopy.

The gold nanoparticle is visualized by electron microscopy, thus enabling correlation of the distribution of fluorescence or light microscopic staining with the macromolecular localization of the gold nanoparticles by electron microscopy.

In addition, reagents are disclosed which incorporate both a redox enzyme such as horseradish peroxidase, and a gold nanoparticle conjugated to an antibody, protein or other targeted biomolecule, in which the proximity of the gold nanoparticle and enzyme provide greater reactivity with metal ions in solution that either alone. When used with autometallographic development or enzyme metallographic development, these combined enzymatic and gold probes provide higher sensitivity for the detection of biological targets on blots, in cells, and in tissues than probes bearing either label alone. Sensitivity may be further increased by incorporation or conjugation of multiple enzymatic and gold labeled probes into polymers, providing for the detection of smaller, lower copy number targets, and the visualization of smaller, repeat-free probes for in situ hybridization.

Combined enzymatic and gold labeled probes were prepared according to the following examples. These include specific combinations of targets, probes, and signal development and amplification procedures. However, the general method includes other combinations not cited specifically herein, including the use of larger gold particles, particles of other metals, other fluorescent or fluorogenic substrates, the use of polymers with different molecular weights, sizes and compositions to those given, and application to other systems and targets including the localization of nucleic acids, enzymes, carbohydrates, proteins, hormones, substrates or substrate analogs, and other biologically significant species.

interacting with solution species, and an outer hydrophilic domain to make the particles water-soluble and biocompatible. Covalently linked 5 and 10 nm probes described previously were stabilized and functionalized using ligands (1) and (2) (below).

Although the following examples focus on detection using light and electron microscopy of biological samples, the probes may also be used to detect non-biological samples, such as pesticides and other chemicals. Furthermore, the signals produced may be detected by direct human or equipment visualization, such as with a camera, without the need for microscopic examination. The metallographic deposits may also be detected by other means, such as reflectance, scattering, and other optical means. The signals developed may also be detected by non-optical means, such as measurement of changes in electrical properties, for example, a change in capacitance, inductance, bridging two or more electrodes to complete a circuit, conductance, resistivity. Mass changes may also be used for detection, such as the alteration of resonant frequency of a quartz crystal which changes with mass, where the deposition of metal on the crystal changes its mass.

Example 1

A combined 1.4 nm Nanogold and horseradish peroxidase conjugate was prepared using commercially available horse radish preoxidase (HRP)-conjugated secondary IgG antibodies. These were labeled using Mono-Sulfo-NHS-Nanogold, prepared by activation of a mono-amino derivative of Nanogold with bis (sulfosuccinimydyl) suberate, BS3. Conjugates were isolated by gel filtration using a Superose-12 column eluted with 0.02 M sodium phosphate buffered 0.15M saline, pH 7.4.

Example 2

Colloidal gold particles may be stabilized, solubilized and chemically functionalized for conjugation to biomolecules using thiol ligands, which have a strong affinity for gold. Stabilization is achieved using ligands with an inner hydrophobic domain to "seal" the gold surface and prevent it from Alternately, the shorter ligands (3), (4) and (5) were used to prepare probes with thinner ligand coatings and provide for smaller conjugate sizes. A 9:1 mixture of (4) and (2) was found to be effective. 3 nm gold was prepared by citrate/tannic acid reduction of tetrachlorauric acid solution, or treatment with sodium thiocyanate. Particles were then stirred with an excess of a 9:1 mixture of (4):(2), then separated by density gradient centrifugation over a 10-30% glycerol gradient followed by gel filtration over a desalting gel (GH25, Milliore) to remove the glycerol. They were then activated by reaction with excess BS3 and mixed in a 3:1 ratio with HRP-conjugated IgG antibody. Products were then separated by density gradient centrifugation over a 10-30% glycerol gradient followed by gel filtration (Superose-12, Pharmacia).

Example 3

A conventional colloidal gold HRP-antibody conjugate was prepared using 5 nm colloidal gold particles prepared by citrate/tannic acid reduction of tetrachloroaurate. The antibody concentration required for stabilization was found by titration followed by sodium chloride challenge using a series of increasing antibody concentrations, taking the concentration at which the conjugate no longer flocculated (i.e. no color change occurred) upon salt addition. The combined gold and peroxidase conjugate was then isolated by centrifugation and pelleting followed by resuspension.

Example 4

A combined 10 nm colloidal gold HRP-antibody conjugate was prepared in the same manner as the combined 5 nm gold and HRP-labeled probe described previously, using 10 nm gold particles prepared by citrate/tannic acid reduction of tetrachloroaurate, using titration followed by sodium chloride challenge to find the optimum antibody concentrations, then isolated by centrifugation and pelleting followed by resuspension.

Example 5

A polymerized combined Nanogold and HRP-antibody conjugate was prepared from the conjugate described in Example 1. This was linked to a 500,000 MW, amino-substituted dextran which was activated for coupling to amines using bis (sulfosuccinimydyl) suberate, BS3, incubated overnight at 4° C. with excess Nanogold and HRP-labeled IgG. Next day, the conjugate was isolated by gel filtration over Superose-12 gel filtration media eluted with 0.02 M sodium phosphate buffer with 0.15 M sodium chloride, pH 7.4.

Example 6

A polymerized combined Nanogold and HRP-antibody conjugate was prepared from the conjugate described in Example 1. This was linked to a 500,000 or 2,000,000 MW dextran which was activated for coupling to amines by oxidation with sodium periodate, thus generating aldehyde groups from 1,2-diols. The oxidized dextran was then incubated overnight at 4° C. with excess Nanogold and HRP-labeled IgG. Next day, the conjugate was isolated by gel filtration over Superose-12 or Superose-6 gel filtration media, eluted with 0.02 M sodium phosphate buffer with 0.15 M sodium chloride, pH 7.4.

Example 7

Combined Nanogold and HRP-Labeled Antibodies

Figure 1:
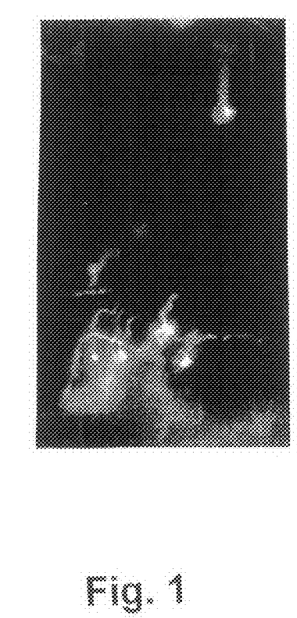
FIG. 1 illustrates the results of a test using horse radish preoxidase (HRP) and Nanogold-labeled IgG with fluorescent tyramides. The polar tube test specimens were incubated for 30 minutes at 32° C. with a 1:200 dilution of the combined Nanogold and HRP-labeled IgG anti-rabbit IgG, prepared by the conjugation of Mono-Sulfo-NHS-Nanogold to the corresponding commercially purchased HRP-IgG, and rinsed three times with TPBS-BSA. Alexa Fluor 488-labeled tyramide (Molecular Probes) was then applied for 10 minutes. Slides were rinsed three times in PBS, and cover glassed (with Dabco). Examination by fluorescence microscopy showed numerous well stained polar tubes.
Figure 2A:
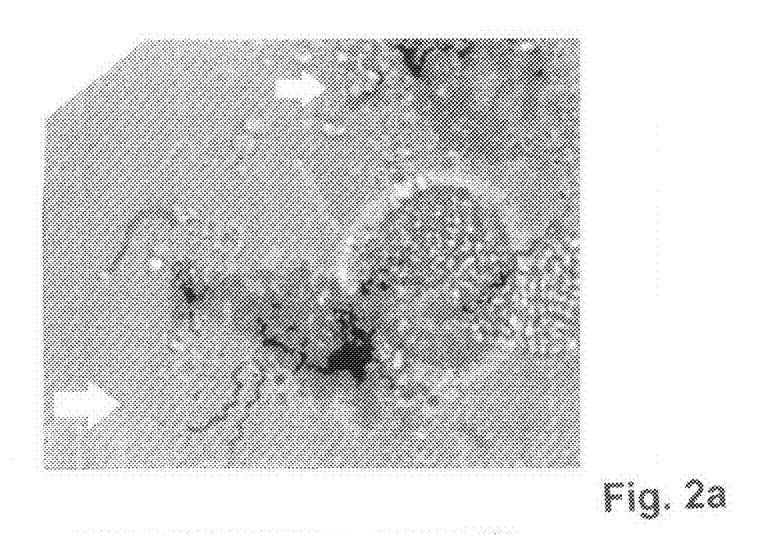
FIGS. 2a and 2b illustrate the results of a test using horse radish preoxidase and Nanogold-labeled IgG with a metallographic substrate. The polar tube test specimens were incubated for 30 minutes at 32° C. with a 1:200 dilution of the combined Nanogold and HRP-labeled IgG, and rinsed three times with TPBS-BSA. Chambers were rinsed three times with deionized water and once with 0.02 M sodium citrate buffer at pH 3.8, decanted, then developed with metallographic substrate similar to a silver enhancement reagent.

Correlative microscopy experiments were conducted in *Encephalitozoon hellem* microsporidian-infected cultured RK-13 cells. RK-13 cultures were grown and infected in NUNC plastic cell culture chamber slides, immunofixed (for electron microscopy), and stored in PBS buffer. Cells were blocked (normal goat serum and bovine serum albumin (BSA) in 0.01% Tween-20-phosphate buffered saline (TPBS)) for 30 minutes at 32° C., rinsed three times (TPBS-BSA), then incubated for 30 minutes at 32° C. in 1:100 anti-*E. hellem* PTP55 antibody, 70 and rinsed three times with TPBS-BSA. Specimens were then stained and examined as follows:

Combined HRP and Nanogold-labeled IgG with fluorescent tyramides: Specimens were incubated for 30 minutes at 32° C. with a 1:200 dilution of the combined Nanogold and HRP-labeled IgG anti-rabbit IgG, prepared by the conjugation of Mono-Sulfo-NHS-Nanogold to the corresponding commercially purchased HRP-IgG, and rinsed three times with TPBS-BSA. Alexa Fluor 488-labeled tyramide (Molecular Probes) was then applied for 10 minutes. Slides were rinsed three times in PBS, and cover glassed (with Dabco). Examination by fluorescence microscopy showed numerous well stained polar tubes (FIG. 2(*a*)).

Figure 2B:
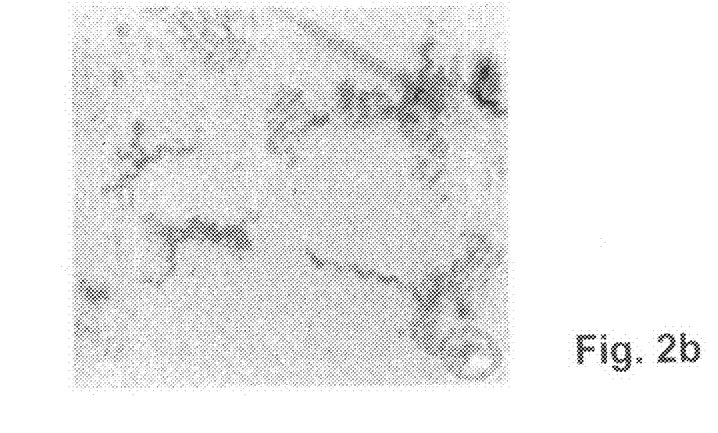

Combined HRP and Nanogold-labeled IgG with Metallographic Substrate: specimens were incubated for 30 minutes at 32° C. with a 1:200 dilution of the combined Nanogold and HRP-labeled IgG, and rinsed three times with TPBS-BSA. Chambers were rinsed three times with deionized water and once with 0.02 M sodium citrate buffer at pH 3.8, decanted, then developed with metallographic substrate similar to a silver enhancement reagent. Two different silver development substrates were tested, one with no modifier, and one containing 15% gum arabic in order to control reaction rate and ensure uniform development. Both procedures resulted in clearly stained polar tubes; with gum arabic, almost no background could be seen, and staining was very clear (FIGS. 2(*b*) and (*c*)).

Figure 3A:
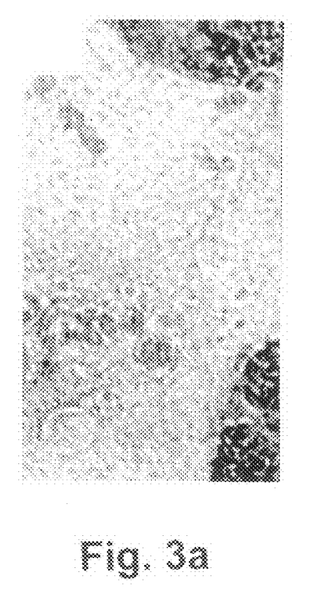
FIGS. 3a, 3b, 3c and 3d illustrate the results of a test using horse radish preoxidase and Nanogold-labeled IgG with silver enhancement. After development with fluorescent tyramide, cover slips were removed, the slides were rinsed twice in TPBS and three times in ultrapure water, then developed with HQ Silver silver enhancement reagent (Nanoprobes; 2×4 minutes).
Figure 3B:
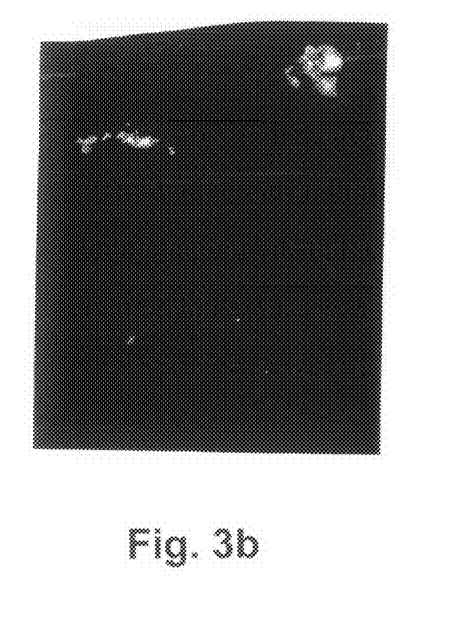
Figure 3C:
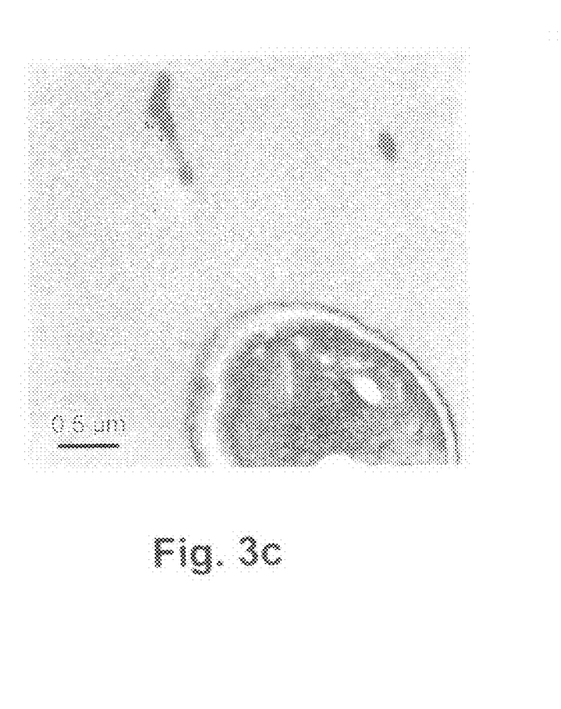
Figure 3D:
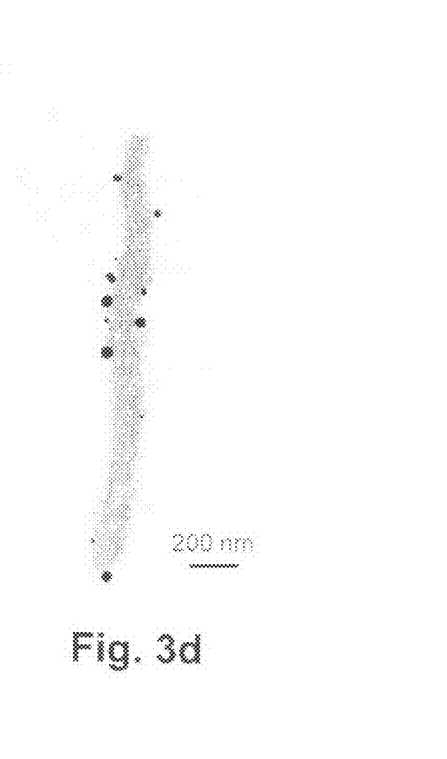

Combined HRP and Nanogold-labeled IgG with Silver Enhancement: following development with fluorescent tyramide, cover slips were removed. Slides were rinsed twice in TPBS and three times in ultrapure water, then developed with HQ Silver silver enhancement reagent (Nanoprobes; 2×4 minutes). This was sufficient to produce faint staining by light microscopy (FIG. 3(*d*)). Reexamination by fluorescence microscopy still showed a clear fluorescent signal (FIG. 2(*e*)). These specimens were then processed for electron microscopy: cover glasses were removed and the slides rinsed in distilled water, dehydrated through a series of ethanol solutions (50%-100%) and infiltrated with Araldite 502 resin (EMS, PA) overnight. Marked areas were covered with BEEM capsules filled with resin, and embedded at 60° C. for 24 hours. Thin sections were cut, placed on copper grids, and stained with uranyl acetate and lead citrate. Samples were examined using an FEI Tecnai 12 transmission electron microscope. The polar tubes were clearly visible and showed specific staining with silver-enhanced Nanogold (FIGS. 2(*f*) and (*g*)).

Example 8

Combined 5 nm Gold and HRP-Labeled Antibodies

Staining experiments were conducted in *Encephalitozoon hellem* microsporidian-infected cultured RK-13 cells, prepared as described in the original application. Staining was conducted following similar protocols, using primary antibodies against PTP-55 or PTP-80, except that a 1:50 dilution of the combined 5 nm gold-HRP probe was used, and a 15 rather than 10 minute incubation with fluorescent tyramides. After light microscope examination, areas of interest were marked on the back of the slides. The cover glasses were removed, and the slides rinsed in distilled water, dehydrated through a series of ethanol solutions (50%-100%) and infiltrated with Araldite 502 resin (EMS, PA) overnight. Marked areas were covered with BEEM capsules filled with resin, and embedded at 60° C. for 24 hours. Thin sections were stained with uranyl acetate and lead citrate, then examined using an FEI Tecnai 12 transmission electron microscope at 80 kV. Results are shown in FIG. 3. Strong and specific polar tube staining was found upon examination by all four microscopic methods: fluorescence microscopy after development with Alexa Fluor 488 tyramides, transmission electron microscopy both with and without development with metallographic silver substrate, and by brightfield light microscopy after development with the silver metallographic substrate. Strong fluorescence was observed even in the presence of 5 nm gold, confirming that this approach overcomes the fluorescence quenching found with combined fluorescent and larger gold antibody conjugates. Staining was consistent with the known distribution for two polar tube proteins, PTP-55 and PTP-80.

Example 9

Combined 10 nm Gold and HRP-Labeled Antibodies

Figure 4A:
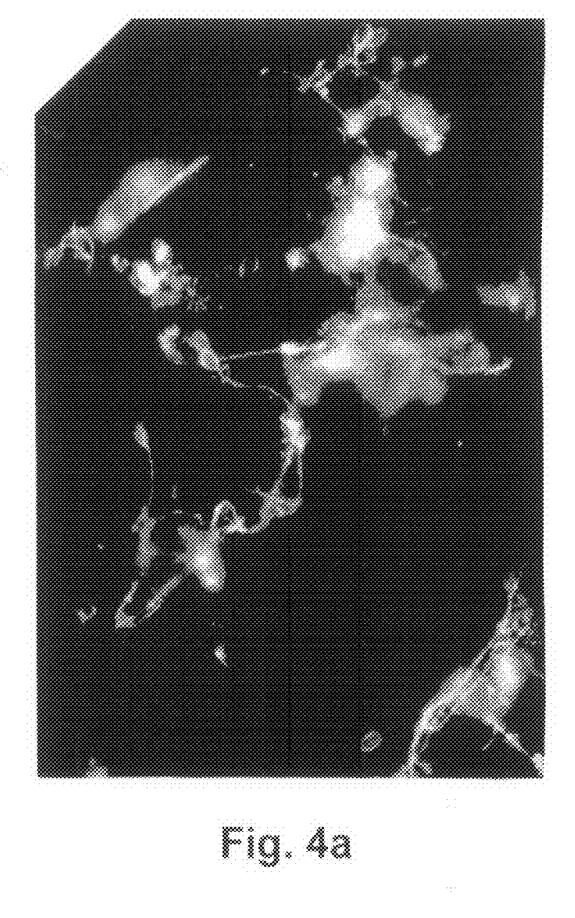

Staining experiments were conducted in *Brachiola algerae* microsporidian-infected cultured RK-13 cells, prepared and processed as described above for the combined 5 nm gold and HRP probes. Cells were blocked (normal goat serum and bovine serum albumin (BSA) in 0.01% Tween-20-phosphate buffered saline (TPBS)) for 30 minutes at 32° C., rinsed three times (TPBS-BSA), then incubated for 30 minutes at 32° C. in 1:100 anti-*E. hellem* PTP80 antibody, rinsed three times with TPBS-BSA, then stained and examined as follows:

Combined HRP and 10 nm gold-labeled IgG with fluorescent tyramides: Specimens were incubated for 30 minutes at 32° C. with a 1:50 dilution of the combined 10 nm gold and HRP-labeled secondary antibody, and rinsed three times with TPBS-BSA. Alexa Fluor 488-labeled tyramide (Molecular Probes) was then applied for 15 minutes. Slides were rinsed three times in PBS, and cover glassed (with Dabco). Examination by fluorescence microscopy showed numerous well stained polar tubes (FIG. 4(a)). This confirms that the method may be extended even to 10 nm gold probes.

Figure 4B:
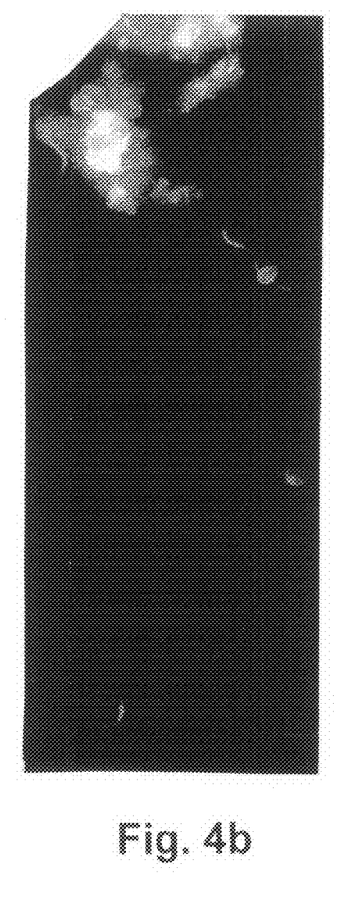
Figure 4C:
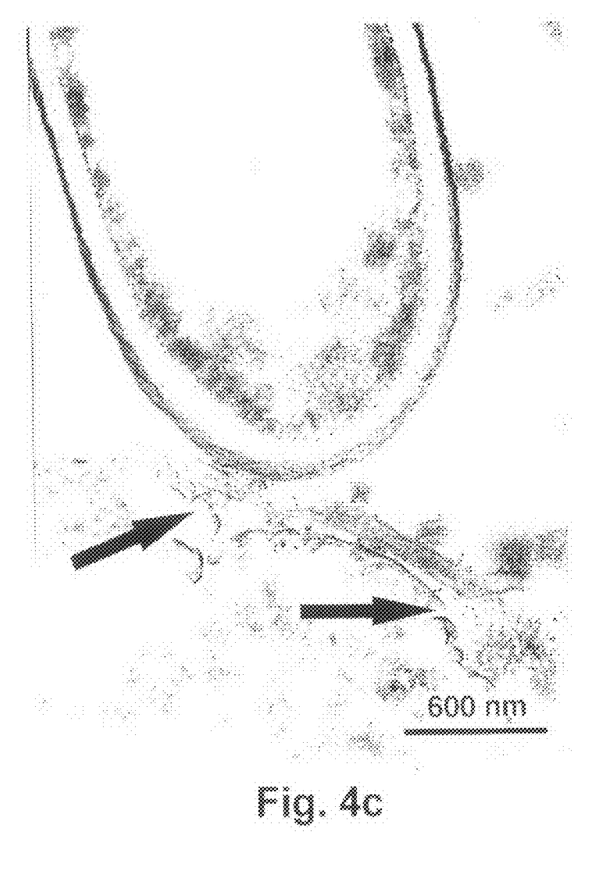
Figure 4D:
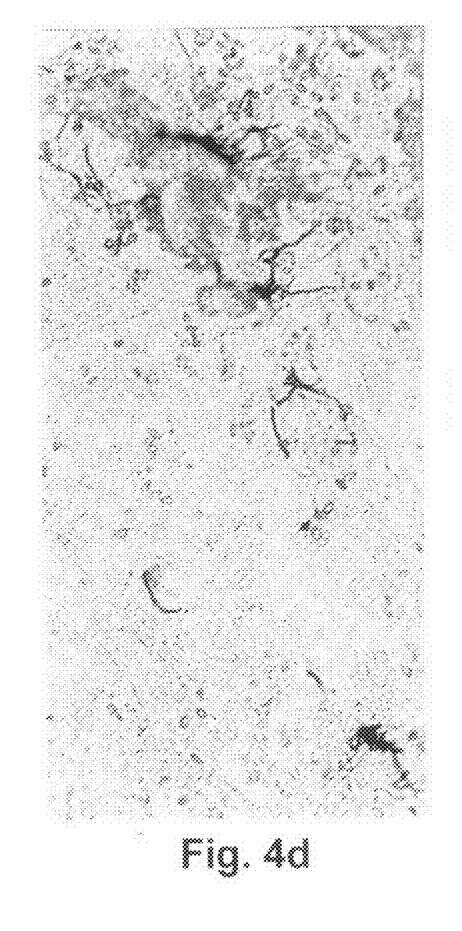
Figure 4E:
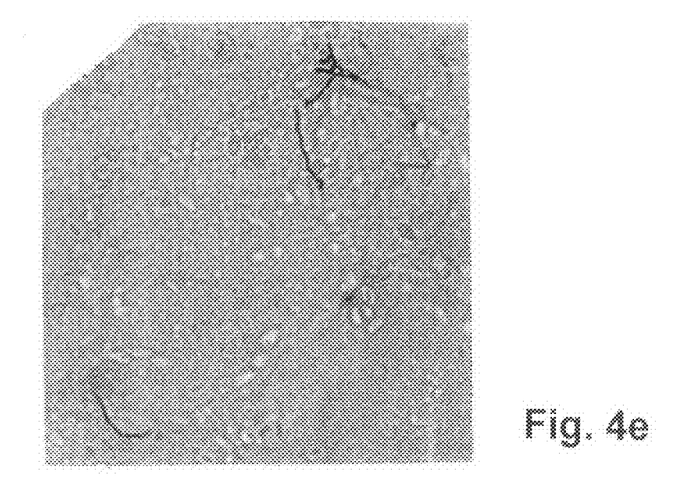
Figure 4F:
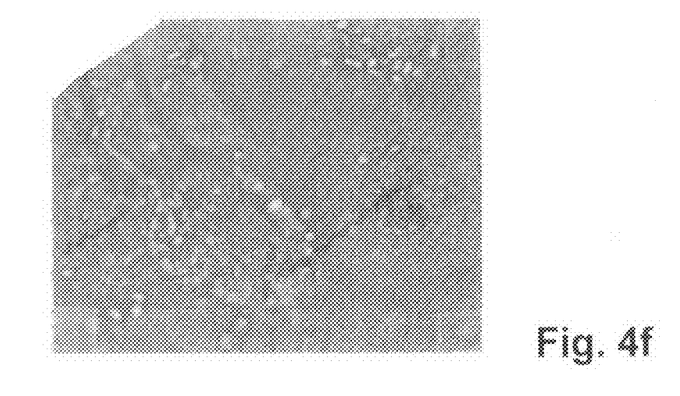
Figure 4G:
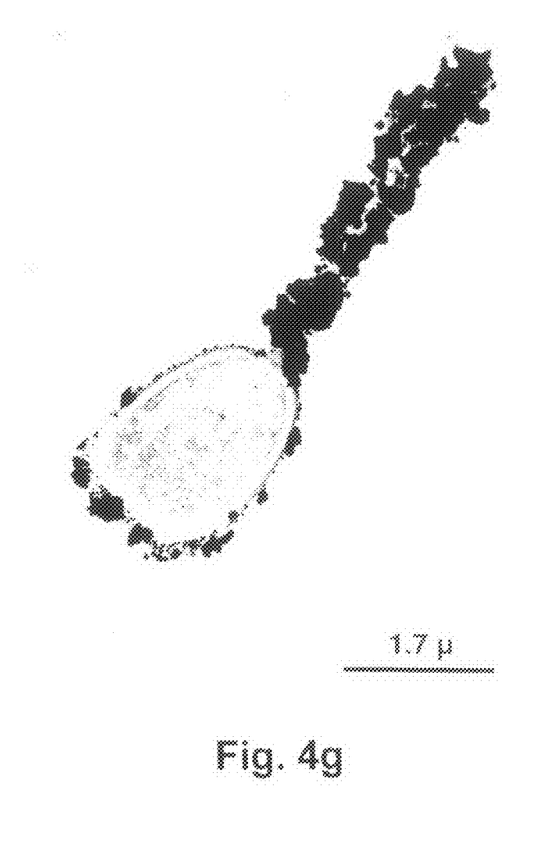
Figure 5:
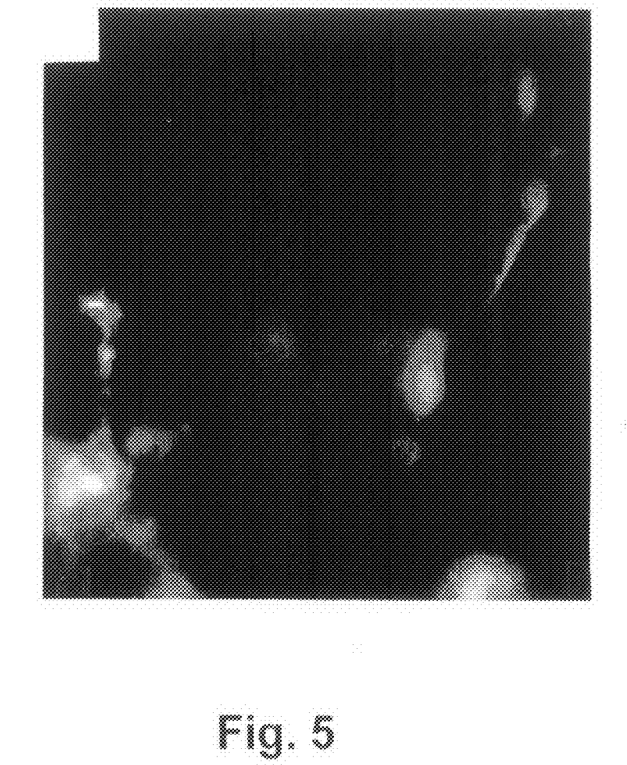
FIG. 5 illustrate the results of a test using horse radish preoxidase and 10 nm gold-labeled IgG with fluorescent tyramides. Specimens were incubated for 30 minutes at 32° C. with a 1:50 dilution of the combined 10 nm gold and HRP-labeled secondary antibody, and rinsed three times with TPBS-BSA. Alexa Fluor 488-labeled tyramide (Molecular Probes) was then applied for 15 minutes. Slides were rinsed three times in PBS, and cover glassed (with Dabco). Fluorescence microscopy clearly shows numerous well stained polar tubes.
Figure 6:
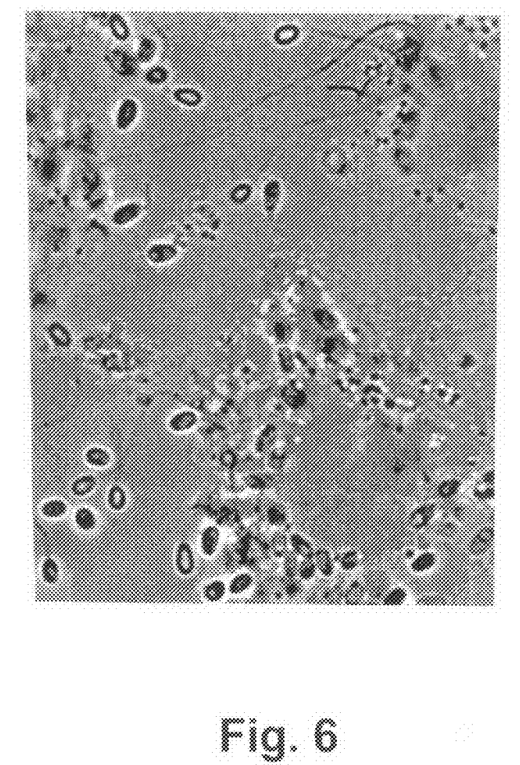
FIG. 6 illustrate the results of a test using horse radish preoxidase and 10 nm gold-labeled IgG with Metallographic Substrate. Specimens were incubated for 30 minutes at 32° C. with a 1:50 dilution of the combined Nanogold and HRP-labeled IgG, and rinsed three times with TPBS-BSA. Chambers were rinsed three times with deionized water and once with 0.02 M sodium citrate buffer at pH 3.8, decanted, then developed with the metallographic substrate. Numerous clearly stained polar tubes were readily visualized with high resolution.

Combined HRP and 10 nm gold-labeled IgG with Metallographic Substrate: specimens were incubated for 30 minutes at 32° C. with a 1:50 dilution of the combined Nanogold and HRP-labeled IgG, and rinsed three times with TPBS-BSA. Chambers were rinsed three times with deionized water and once with 0.02 M sodium citrate buffer at pH 3.8, decanted, then developed with the metallographic substrate. Numerous clearly stained polar tubes were readily visualized with high resolution (FIG. 4(b)).

Example 10

Increased Sensitivity on Blots

The preparation and immunoblot testing of combined 1.4 nm Nanogold and horseradish peroxidase-conjugated streptavidin confirmed that incorporating both labels can provide significantly higher sensitivity than either alone. Streptavidin-HRP was labeled using Mono-Sulfo-NHS-Nanogold, prepared by activation of a monoamino derivative of Nanogold with bis (sulfo-succinimydyl) suberate, BS3. Conjugates were isolated by gel filtration using a Superose-12 column eluted with 0.02 M sodium phosphate buffered 0.15M saline, pH 7.4.

A nitrocellulose membrane was simmered in gently boiling water for 15 minutes. Tenfold serial dilutions of a biotinylated sheep anti-mouse IgG antibody from 100 ng/µL to 0.01 pg/µL were applied to the membrane surface using a 1-microliter capillary. The membrane was air-dried for 15 minutes, then blocked with a solution of 4% bovine serum albumin in phosphate-buffered saline (PBS: 0.02 M sodium phosphate buffer with 0.15 M sodium chloride at pH 7.4) at 37° C. for 30 minutes, then incubated with the combined Nanogold and HRP-labeled conjugate. Two comparison experiments were run:

Development with enzyme metallography substrate, in parallel with streptavidin-HRP detection.

Development with enzyme metallography substrate and silver enhancement (Ll Silver, Nanoprobes), in parallel with detection of the same target using Nanogold-streptavidin developed using Ll Silver.

The combined Nanogold and HRP-labeled probe shows an increase in detection sensitivity of one to two orders of magnitude compared with either an enzymatic probe detected using enzyme metallography, or a Nanogold-labeled probe detected with silver enhancement.

The sensitivity of the polymerized probe was further demonstrated in a Western blot experiment. The probe comprising a 500,000 MW dextran linked to both 1.4 nm gold particles and enzymatic labels was evaluated in Western Blot experiments for the detection of HER2 protein in Skbr3 cell lysates using 4B5 primary antibody from Ventana, and OP15 primary antibody. These were then detected by incubation for 60 minutes with 1:250 and 1:25 dilution, respectively, of the polymerized Nanogold-HRP antibody, then developed with the metallographic substrate used for enzyme metallography. Results are shown in FIG. 7. From the comparison of (c) and (d), it can be seen that the polymerized enzymatic and gold probe yielded equivalent sensitivity to the chemiluminescent detection.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A composite probe, comprising:
    at least one directing agent for attaching the composite probe to a target in a test sample;
    at least one nanoparticle conjugated to the at least one directing agent, the at least one nanoparticle comprising a plurality of metal atoms; and
    an enzyme, chemically linked to the at least one directing agent, for reacting with an enzyme substrate after the composite probe is bound to the target.

2. The composite probe of claim 1 further comprising a polymer member, the polymer member having a plurality of nanoparticles bound thereto.

3. The composite probe of claim 1 wherein the enzyme substrate is a fluorescent or fluorogenic material.

4. The composite probe of claim 3 wherein the fluorescent or fluorogenic material is a fluorescent tyramide.

5. The composite probe of claim 1 wherein the enzyme substrate is a chromogenic material.

6. The composite probe of claim 1 wherein the enzyme substrate is a metallographic material.

7. The composite probe of claim 6 wherein the metallographic material is an oxidizing agent, a reducing agent and a metal ion source, and at least some metal ions of the metal ion source are reduced to a zero oxidation state.

8. The composite probe of claim 1 wherein the plurality of metal atoms are gold metal atoms, and the at least one nanoparticle has a diameter of 0.8 nm to 40 nm.

9. The composite probe of claim 8 wherein the directing agent comprises an antibody, an antibody fragment, a single chain antibody, a peptide, a drug, a nucleic acid, an enzyme substrate for an enzyme present in the test sample, an organic compound, or a protein.

10. The composite probe of claim 9 wherein the enzyme substrate is a substrate for a redox active enzyme.

11. The composite probe of claim 1 wherein the plurality of metal atoms are gold metal atoms, and the at least one nanoparticle has a diameter of from about 3 nm to about 10 nm.

12. A method of detecting a target in a sample comprising:
    exposing the sample to the composite probe of claim 1;
    treating the sample with an enhancement or development solution to deposit at least one of a fluorophore, a chromogen, or a metal;
    performing at least one test to detect fluorescence produced by the deposited fluorophore, color produced by the deposited chromogen, the metal atoms of the nanoparticle, or the deposited metal.

13. The method of claim 12 wherein the fluorophore is a fluorescent or fluorogenic substrate and the test comprises examining the sample with fluorescence microscopy or other fluorescent detection device or method.

14. The method of claim of claim 13 further comprising examining the sample by electron microscopy or other metallic cluster particle or deposit detection or visualization method.

15. The method of claim 12 wherein the metal is a metallographic substrate and the test comprises examining the sample with light microscopy, electron microscopy, or other microscopical method for detecting or visualizing deposited metal.

16. The method of claim 12 wherein the metal is an autometallographic reagent or an enzyme metallographic substrate and the test comprises examining the sample with brightfield light microscopy.

17. The method of claim 12 wherein the test is electron microscopy, brightfield microscopy, fluorescent microscopy, directly visible signal without microscopy, or electrical detection.

18. The method of claim 12 wherein the test is examination by direct optical detection or by an optical recording device.

19. The method of claim 12 wherein the test is examination of electrical properties of the deposited metal.

20. The method of claim 12 further comprising immobilizing the target on a membrane or other surface.

21. A method of detecting a target in a sample comprising:
exposing the sample to the composite probe of claim 2;
treating the sample with an enhancement or development solution to deposit at least one of a fluorophore, a chromogen, or a metal;
performing at least one test to detect fluorescence produced by the deposited fluorophore, color produced by the deposited chromogen, the metal atoms of the nanoparticle, or the deposited metal.

* * * * *